(12) United States Patent
Duchamp

(10) Patent No.: US 6,626,874 B1
(45) Date of Patent: Sep. 30, 2003

(54) ANTICOAGULANT INTERNALLY COATED NEEDLE

(75) Inventor: Jacky G. Duchamp, Keene, NH (US)

(73) Assignee: Portex, Inc., Keene, NH (US)

(*) Notice: Subject to any disclaimer, the term of this patent is extended or adjusted under 35 U.S.C. 154(b) by 136 days.

(21) Appl. No.: 09/714,288

(22) Filed: Nov. 17, 2000

(51) Int. Cl.$^7$ .................. A61M 25/00; A61M 5/32; A61M 5/178; B05D 1/40; B06B 1/00

(52) U.S. Cl. .................. 604/266; 604/265; 604/192; 604/198; 604/199; 604/164.08; 427/480; 427/600

(58) Field of Search .................. 604/265, 264, 604/266, 192, 198, 199, 164.08; 427/2.13, 2.28, 475, 476, 477, 478, 479, 480, 560, 565, 600

(56) References Cited

U.S. PATENT DOCUMENTS

| | | | |
|---|---|---|---|
| 3,610,226 A | | 10/1971 | Alblsser |
| 4,087,567 A | * | 5/1978 | Sullivan .................. 427/2.13 |
| 4,133,304 A | | 1/1979 | Bailey |
| 4,327,722 A | | 5/1982 | Gorshong et al. |
| 4,409,990 A | | 10/1983 | Mileikowsky |
| 4,424,817 A | | 1/1984 | Williams |
| 4,479,799 A | | 10/1984 | Thiel |
| 4,529,614 A | * | 7/1985 | Burns .................. 215/DIG. 3 |
| 4,572,210 A | | 2/1986 | McKinnon |
| 4,653,511 A | | 3/1987 | Goch |
| 4,657,028 A | * | 4/1987 | Rich et al. .................. 600/576 |
| 4,808,449 A | * | 2/1989 | McAlister .................. 422/100 |
| 4,850,998 A | | 7/1989 | Schoendorfer |
| 4,876,126 A | * | 10/1989 | Takemura et al. .................. 427/2.1 |
| 5,403,304 A | | 4/1995 | Ishida |
| 5,417,681 A | | 5/1995 | Miyake et al. |
| 5,584,816 A | | 12/1996 | Gyure et al. |
| 5,693,022 A | * | 12/1997 | Haynes .................. 604/192 |
| 5,788,678 A | | 8/1998 | Van Antwerp |
| 5,801,057 A | | 9/1998 | Smart et al. |
| 5,915,384 A | | 6/1999 | Grossman et al. |
| 6,187,370 B1 | * | 2/2001 | Dinh et al. .................. 264/28 |

FOREIGN PATENT DOCUMENTS

EP        0 109 970        6/1984

* cited by examiner

*Primary Examiner*—William C Doerrler
*Assistant Examiner*—Filip Zec

(57) ABSTRACT

To prevent blood from clotting or being diluted (which causes inaccuracy in the measurement of the characteristics of blood drawn from a patient), a needle assembly has the interior portion of its cannula and at least one portion of its hub covered by a dry coat of anticoagulant. To provide the dry coat of anticoagulant onto the interior surfaces of the cannula and the hub, a liquid anticoagulant is atomized thereto so that an even coat of the anticoagulant is provided to the interior surfaces of the cannula and hub. The volume and concentration of the anticoagulant atomized to the inside of the needle assembly are controlled as the liquid anticoagulant is ultra-sonically atomized to the interior portion of the needle assembly.

9 Claims, 1 Drawing Sheet

ANTICOAGULANT INTERNALLY COATED NEEDLE

FIELD OF THE INVENTION

The present invention relates to blood drawing devices, and more particularly a blood drawing device that has a needle, or cannula, internally coated with an anticoagulant so that when the needle is used to puncture the artery or vein of a patient, blood that flows through the needle is clot free.

BACKGROUND OF THE INVENTION

In the medical field, in addition to being known as one of the more important medications, heparin is used to inhibit coagulation of blood drawn for blood gas analysis and other laboratory tests. In conventional commercial blood drawing tubes or syringes, the final concentration of heparin is known to be about 3–200 units/ml. This concentration of heparin is by far and away sufficient to anticoagulate blood drawn from a patient.

Based on a study carried out by the departments of pathology, biochemistry and pediatrics of the University of Colorado Health Sciences Center in Denver, Colo. the concentration of heparin (bovine sodium heparin) necessary to inhibit clotting was found to be 0.6 and 0.75 units/ml of plasma and 0.4 and 0.6 units/ml of whole blood. No visual clots or instrumentation interference due to micro-clots were observed in whole blood anticoagulated with a minimum of 1.0 unit/ml of heparin after 20 minutes at room temperature or 75 minutes at 4° C. At 4° C., the minimum heparin concentration to inhibit whole blood from clotting for over 4 hours was 0.75 unit/ml.

However, since most manufacturers of blood drawing devices use some form of dry heparin (vaporized or lyophilized) in the body of the device, occasional premature clots particularly inside the inner surface of the cannula would occur. So, too, because of the different degrees of roughness of the inner surface of the cannula and the uniqueness of the clotting factors which vary from individual to individual, it is not uncommon for micro-clots to form in the blood prior to the blood reaching the bulk of the heparin in the blood storage device This phenomenon does not occur in blood drawing devices that contain a form of liquid heparin. This is due to the fact that as the excess liquid heparin is expelled prior to use (by the user pushing the plunger of the syringe in the direction of the needle), the inner surface of the cannula is indirectly coated, thereby enabling the blood to be in contact with the anticoagulant as soon as it is drawn from the patient. But, a problem does arise with the use of such blood drawing device because of the dilution effect that liquid heparin has on the blood drawn, as the accuracy of the measurement of the various components in the blood drawn from the patient is affected by the blood having been diluted with the liquid heparin.

In view of the disadvantages of the conventional types of blood drawing devices coated with dry heparin and liquid heparin, there is therefore a need for a blood drawing device coated with an anticoagulant that will not cause micro-clots or be affected by any dilution effect of the blood withdrawn from the patient. Putting it differently, there is a need for a blood drawing device that would not adversely influence the analysis of pH/blood gases co-oximetry, electrolytes and metabolites of drawn blood.

SUMMARY OF THE INVENTION

To overcome the disadvantages of the prior art blood drawing devices, the present invention blood drawing device has the interior or inner surface of its needle, or cannula, atomized with a liquid anticoagulant by an ultrasonic atomization process. The thus atomized cannula is then dried, either by air or by heat so that the interior surface thereof is coated with a layer of anticoagulant at a concentration that comports with the above-noted study done by the University of Colorado Health Sciences Center. The thus anticoagulated cannula of the present invention can be used with a syringe, or container, that is fitted with an air bubble removable filter such as the FILTER-PRO™ of the assignee, The syringe can also have attached thereto the needle protection sheath (NEEDLE-PRO™) of the assignee.

An objective of the present invention blood drawing device is to prevent any clotting effect that may occur when a cannula is used with a blood withdrawing device.

Another objective of the present invention is to provide a blood drawing device having a cannula that does not require to be coated by any liquid heparin just prior to its being used.

Yet another objective of the present invention is the provision of a blood drawing device that has a stable, non-reactive coating of an anticoagulant already formed in the inner surface of its cannula, so that the device has an extended period of shelf store life and can be used right from the package.

BRIEF DESCRIPTION OF THE DRAWINGS

The above-mentioned objectives and advantages of the present invention will become more apparent and the invention itself will be best understood by reference to the following description of an embodiment of the invention taken in conjunction with the accompanying drawings, wherein.

DETAILED DESCRIPTION OF THE INVENTION

Figure 1:
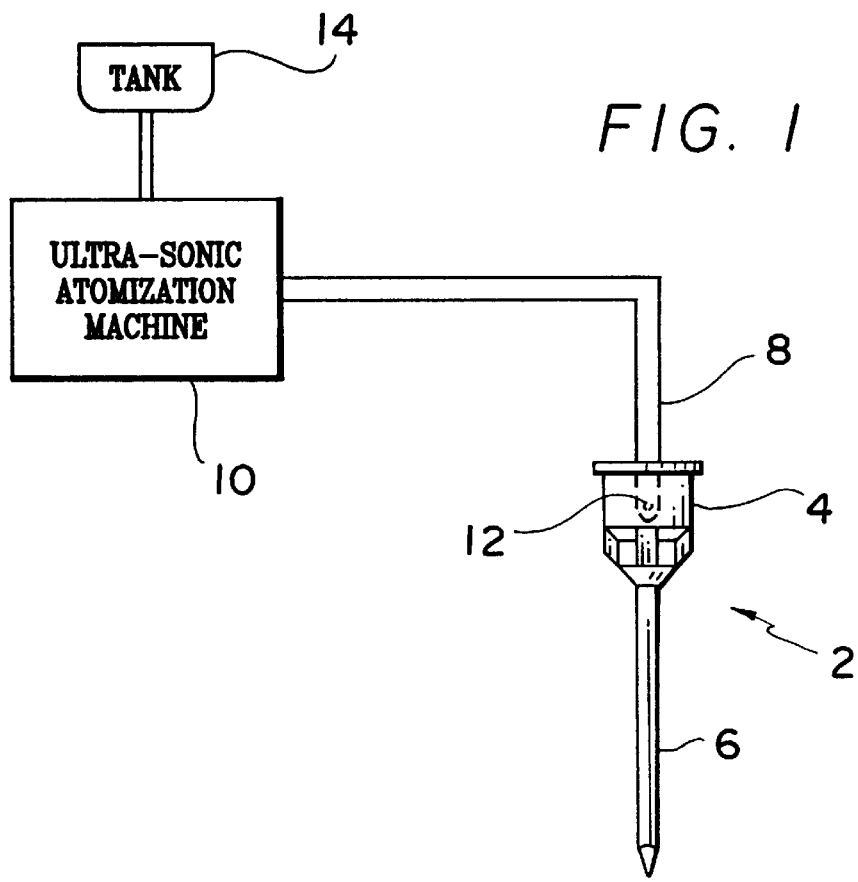
FIG. 1 is an illustration of a needle of the present invention and its being atomized with a liquid anticoagulant.
Figure 2:
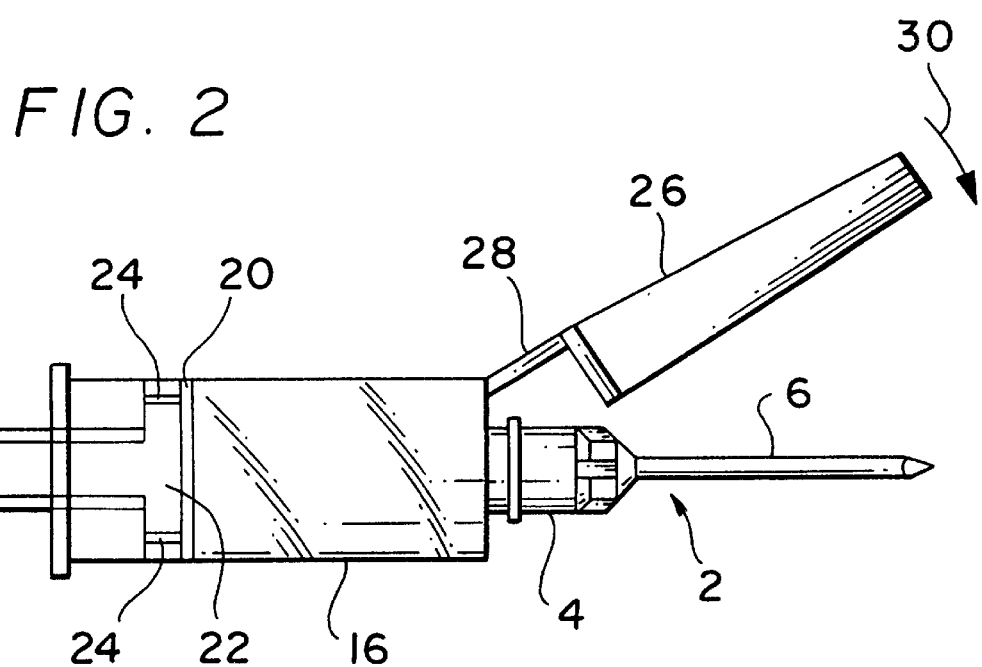
FIG. 2 is a side view of a blood drawing device of the present invention which includes a semi-cut away cross-sectional view of a syringe mated to the hub of a needle assembly of the present invention.

With reference to FIG. 1, the present invention needle assembly 2 is shown to include a hub 4 and a cannula 6 made of stainless steel. In the preferred embodiment, the stainless steel used for cannula 6 is the 304 type. However, other types of known stainless steel are also suitable for use.

Hub 4 of needle assembly 2 may be a color-coated translucent hub. In the preferred embodiment, needle 6 may be of various sizes including, for example, Regular (A), Intermediate (IN), and all short (B) type needles.

As further shown in FIG. 1, the inner surface of needle assembly 2 is atomized by a liquid anticoagulant, which may be an aqueous solution of heparin provided by a needle tube 8 output from an ultra-sonic atomization machine 10. In particular, the liquid anticoagulant is dispensed or sprayed from at least one hole, such as 12, provided at the tip of needle tube 8. For the instant invention, ultra-sonic atomization machine 10 in essence is comprised of two components, an atomizer machine made by the Ivek Corporation of Massachusetts having model number 2325 and a pump made by the Digispense Corporation having model number 1586. Note that the liquid anticoagulant being provided to ultra-sonic atomization machine 10 is stored in a pressure tank 14. The amount of liquid anticoagulant being pumped from ultra-sonic atomization machine 10 can be regulated, both in terms of its volume and concentration, so that the appropriate amount of anticoagulant is atomized to at least one portion of the interior surface of hub 4 and the interior surface of cannula 6.

In the preferred embodiment, note that the liquid anticoagulant is an aqueous solution of heparin which is made with sodium heparin powder mixed with ionized water. However, other types of known anticoagulant substances and associated solvent solutions are also suitable for use with the present invention. These include ammonium heparin, zinc heparin, calcium heparin, low molecular weight heparin, lithium heparin, benzalkonium heparin, dermatan heparin, heparin fragments, and heparin peptidoglycan associated (or not associated) under a calcium neutralized form and/or an electrolyte balanced form with de-ionized water, methylene chloride, isopropanol, and 50:50 (v/v) toluene-petroleum ether. Further note that any combinations of the different elements and substances mentioned hereinabove are also suitable for use in the present invention as the liquid anticoagulant.

As noted above, the ultra-sonic atomization machine 10 determines the volume and/or the concentration of the liquid anticoagulant to be atomized to needle assembly 2. The volume of the anticoagulant dispensed in each needle assembly must take into account the length of the needle, and the final anticoagulant concentration that is desired, as for example between 0–200 units/ml per needle. The atomization process is conventional and need not further be discussed. However, note that machine 10 dispenses the liquid anticoagulant by ultrasonic atomization, so that the liquid anticoagulant being coated onto the inner surfaces of hub 4 and needle 6 is provided as an even patterned spray, with sufficiently small droplet size and uniformity. Further note that in addition to ultra-sonic atomization, other types of atomizers may also be used. These include pressure nozzles (hydraulic), two-fluid nozzles (pneumatic), and rotary devices such as spinning cups, disks, or vaned wheels.

The needle assembly 2 of the instant invention, to be useful, also needs to have its anticoagulant coat to be in a stable state. This means that the coat of anticoagulant in the interior portion of the needle assembly 2 has to be dry, so that all liquid in the anticoagulant has evaporated and that the residual anticoagulant coated onto the interior portions of the needle assembly is crystallized. This drying process can be effected in an oven or air dried. Other types of known drying process are also suitable for the instant invention. Some of these conventional processes include using, for example, continuous and batch dryers, infrared or radiant heat dryers, dielectric heat dryers, and continuous and batch indirect dryers. By providing a dry coat of anticoagulant inside the needle assembly, no corrosion due to contact between any liquid (or condensation) to the metal surface of the cannula would occur.

An example of the process of atomization of liquid anticoagulant to the interior portion of the needle assembly 2 is given herein. For the exemplar process, 8 $\mu$l of sodium heparin solution was dispensed inside hub 4 of three categories of needles (22×1"g, 23×1"g, and 25×⅝"g). The optimum concentration for the heparin solution was found to be 10 g/l (or equivalent to 2595 units), After the different needles were dried for example by drying 10 minutes at 19° in an enclosed oven, 4–5 USP units of heparin per needle per ml was recovered, either by an atomic absorption sodium ion study, or by USP potency assay, both processes being conventional and need not be discussed further herein.

With reference to FIG. 2, the present invention needle assembly 2 is shown to mate by means of its hub 4, to a syringe 16. Syringe 16 acts as a container to which blood withdrawn from a patient per cannula 6 is collected, As discussed above, by coating the interior surface of cannula 6, and at least a portion of the interior surface of hub 4, clots, micro-clots or otherwise, are prevented from occurring while the blood transits from the patient through cannula 6 and hub 4, to syringe 16.

To ensure that air bubbles that may be in the blood are removed from syringe 16, the tip of plunger 18 of syringe 16 is fitted with either a hydrophilic or hydrophobic filter 20. Such filter may be the FILTER PRO™ used by the assignee company of the instant invention. Moreover, instead of being at the end of plunger 18, filter 20 may be fitted within a space at end portion 22 of plunger, so that its end face does not come into direct contact with the withdrawn blood. To enable air bubbles to escape from syringe 16, a number of passages, such as 24, may be provided to the end portion of syringe 18, so that as the syringe is filled with blood, any air bubbles therein are forced out into the environment via air passages 24. This is of course due to the fact that air filter 20 has the characteristic of allowing air to pass but blocking the passage of liquids.

Another attribute of the blood drawing device shown in FIG. 2 is a needle protection sheath 26 that is pivotally attached or connected to syringe 16 by means of a living hinge 28. The construction and operation of protection sheath 26 is given in U.S. Pat. No. 5,232,455, the disclosure of which being incorporated by reference herein. In brief, after usage, the contaminated cannula 6 is prevented from being exposed to the environment by the user pivoting needle protection sheath 26 in the direction of arrow 30 so that sheath 26 comes into alignment with cannula 6. A hook, not shown, or other means in sheath 26 (or coacting with hub 4 of needle assembly 2) fixedly retains cannula 6 relative to sheath 26 once sheath 26 has been pivoted into alignment with cannula 6.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only by the spirit and scope of the appended claims.

What is claimed is:

1. A method of manufacturing a non-clottable needle, comprising the steps of:

depositing a liquid anticoagulant to the interior surface of a needle; and drying said liquid anticoagulant to fore a layer of crystallized anticoagulant at the interior surface of said needle.

2. Method of claim 1, wherein said depositing step comprises atomizing said liquid anticoagulant to the interior surface of said needle.

3. A method of manufacturing a non-clottable needle, comprising the steps of:

depositing a liquid anticoagulant to the interior surface of a needle;

drying said liquid anticoagulant to form a layer of crystallized anticoagulant at the interior surface of said needle;

extending said needle from a hub; and depositing said anticoagulant to at least one portion of the interior surface of said hub.

4. Method of claim 1, further comprising the steps of:

mating said needle to a syringe; and flexibly coupling a sheath to said syringe, said sheath pivotable to fixedly envelop said needle.

5. A method of manufacturing a non-clottable needle, comprising the steps of:
   depositing a liquid anticoagulant to the interior surface of a needle;
   drying said liquid anticoagulant to form a layer of crystallized anticoagulant at the interior surface of said needle; and
   drying said anticoagulant by air or by heat.

6. Method of claim 1, wherein said anticoagulant comprises a heparin substance, and wherein said depositing step comprises the step of:
   atomizing said heparin substance to the interior surface of said needle via ultra-sonic atomization.

7. Method of claim 1, further comprising the step of:
   depositing said anticoagulant to the interior surface of said needle in a volume and/or concentration corresponding to the length of said needle.

8. Method of claim 1, wherein said depositing step comprises the step of:
   atomizing the interior surface of said needle with lithium heparin powder mixed with de-ionized water.

9. Method of claim 1, wherein said depositing step comprises the step of:
   atomizing the interior surface of said needle with any of ammonium heparin, zinc heparin, calcium heparin, low molecular weight heparin, sodium heparin, benzalkonium heparin, dermatome heparin, heparin fragments, and various forms of heparin peptidoglycan.

* * * * *

UNITED STATES PATENT AND TRADEMARK OFFICE
CERTIFICATE OF CORRECTION

PATENT NO. : 6,626,874 B1
DATED : September 30, 2003
INVENTOR(S) : Jacky Duchamp It is certified that error appears in the above-identified patent and that said Letters Patent is hereby corrected as shown below:

<u>Column 4,</u>
Line 50, delete "fore" and insert -- form --.

Signed and Sealed this

Twenty-third Day of December, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,626,874 B1
DATED         : September 30, 2003
INVENTOR(S)   : Jacky G. Duchamp It is certified that error appears in the above-identified patent and that said Letters Patent is hereby corrected as shown below:

<u>Title page,</u>
Insert Items:
--      Related U.S. Application Data
[63] Divisional application of Ser. No. 09/044,149, March 19, 1998, abandoned. --; and
-- [74] *Attorney, Agent or Firm* - Louis Woo --

Signed and Sealed this

Seventeenth Day of February, 2004

JON W. DUDAS
*Acting Director of the United States Patent and Trademark Office*